United States Patent [19]

Suzuki

[11] 3,956,318

[45] May 11, 1976

[54] HYDROGENATION OF EPOXIDES

[75] Inventor: Shigeto Suzuki, San Francisco, Calif.

[73] Assignee: Chevron Research Company, San Francisco, Calif.

[22] Filed: Jan. 29, 1975

[21] Appl. No.: 545,253

[52] U.S. Cl. .................. 260/346.1 R; 260/348 R
[51] Int. Cl.² ............................. C07D 307/08
[58] Field of Search .......... 260/346.1, 635 E, 617 R

[56] References Cited
UNITED STATES PATENTS 2,525,672  10/1950  Heilbron et al. ............... 260/346.1

*Primary Examiner*—Harry I. Moatz
*Attorney, Agent, or Firm*—G. F. Magdeburger; John Stoner, Jr.; T. G. DeJonghe

[57] ABSTRACT

A process for producing a substituted tetrahydrofuran which comprises contacting an epoxide with molecular hydrogen and a Group VIII metal hydrogenation catalyst at a temperature between 50° and 250°C and a pressure between 10 and 5000 psig, wherein the contacting is carried out in the liquid phase and in the presence of a protonic acid, and the epoxide has the formula

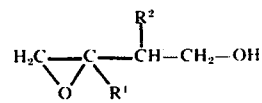

wherein R¹ is a methyl, ethyl, propyl or butyl group and wherein R² is hydrogen, methyl, ethyl, propyl or butyl.

8 Claims, No Drawings

HYDROGENATION OF EPOXIDES

BACKGROUND OF THE INVENTION

The present invention relates to the conversion of an epoxide to a substituted tetrahydrofuran by hydrogenation in the presence of an acid.

The cleavage of epoxides to make new compounds containing a hydroxyl group is in general known in the art. See, for example, Morrison & Boyd, "Organic Chemistry," 2nd Ed., at pp. 877–992.

A Kotz and K. Righter in an article in J. Prakt. Chem. [2] 111, 373 (1925) disclose hydrogenation of an epoxide to obtain a secondary alcohol, as follows:

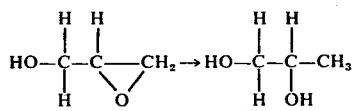

Park and Fuchs state in *J. Org. Chem.*, January 1957, at page 93: "Only a few oxides with electron-withdrawing groups have been hydrogenated, and a secondary alcohol is always produced. Glycidol, epichlorohydrin, and butadiene dioxide are reduced to 1,2-propanediol, 1-chloro-2-propanol, and 2,3-butanediol, respectively, as the main product."

Searles and Butler in JACS, Vol. 76, p. 56 (1954), disclose reduction of 1-chloro-2,3-epoxy propane using hydrogen and a nickel catalyst. The product obtained is 1-chloro-2-propanol, that is, the epoxy group was reduced to result in the OH group being on the secondary rather than the primary carbon atom.

However, Newman, Underwood and Renoll, in JACS, Vol. 71, p. 3362 (1949) disclose reduction of 1,2-epoxy decane using a nickel catalyst to obtain primary decane alcohol.

French Pat. No. 845,305 discloses the conversion of 1,4-butylene glycol or its alkylated products to tetrahydrofurans. According to the patent, at 250°–350°C, or with a catalyst of alkaline nature such as Na$_2$PO$_4$, even at 400°–450°C, one mol of water is eliminated with the resultant formation of tetrahydrofurans.

SUMMARY OF THE INVENTION

According to the present invention a process is provided for producing a substituted tetrahydrofuran, which process comprises contacting, in the liquid phase and in the presence of a protonic acid, an epoxide of the formula

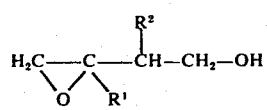

wherein R$^1$ is a methyl, ethyl, propyl, or butyl group and wherein R$^2$ is hydrogen, methyl, ethyl, propyl, or butyl, in a reaction zone with molecular hydrogen and a Group VIII metal hydrogenation catalyst at a temperature between 50° and 250°C and a pressure between 10 and 5000 psig.

Preferably R$^1$ is methyl.

Preferably R$^2$ is hydrogen or methyl.

The substituted tetrahydrofuran products of the present invention are in general useful in those areas in which tetrahydrofuran is useful — for example, in polymerization to obtain fibers and as a solvent.

Substituted tetrahydrofurans can be reacted with ammonia at elevated temperature to form substituted pyrrolidines. In solvent uses for tetrahydrofuran where lower volatility is desirable, the substituted tetrahydrofurans are advantageous in that they are higher boiling than tetrahydrofuran. Tetrahydrofuran boils at 66°C, whereas 3-methyl-tetrahydrofuran boils at 86°–87°C and 3,4-dimethyl-tetrahydrofuran boils at 107.5°–108.5°C. Thus, the substituted tetrahydrofurans can advantageously be used as solvents for organic compounds at elevated temperatures.

Among other factors, the present invention is based on my surprising finding that in the hydrogenation process of the present invention epoxides are not converted to alcohols but instead are converted to substituted hydrofurans.

Preferably the temperatures used in the reaction zone of the process of the present invention are 100° to 150°C, and preferably the pressure is between 100 and 1,000 psig.

A metal hydrogenation catalyst is used in the process of the present invention, and preferably the catalyst comprises a Group VIII metal, i.e., iron, cobalt, nickel, ruthenium, rhodium, palladium, osmium, iridium or platinum. Particularly preferred Group VIII metal components for the hydrogenation catalyst are nickel, palladium or platinum. The Group VIII metal can be present in the catalyst in elemental or reduced form, or it may be present in compound form, such as in the oxide or sulfide form. Preferably the metal hydrogenation component is supported on a carrier, such as porous carbon or an inorganic refractory support such as silica, magnesia, zirconia, alumina, or mixtures of two or more of the preceding inorganic refractory supports.

Preferred epoxide feeds for the process of the present invention and the resulting substituted tetrahydrofuran product are shown in the equations below:

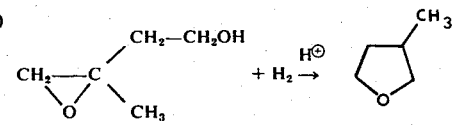

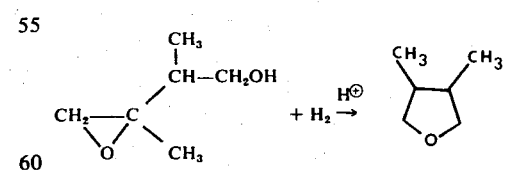

These epoxides may be obtained by the reaction of an unsaturated alcohol with a peracid, as illustrated in the reactions below:

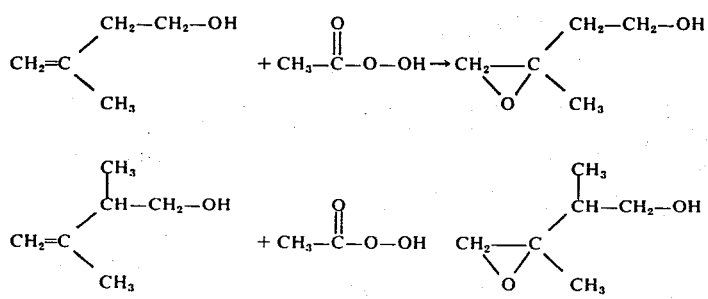

Unsaturated alcohols for use in forming the epoxides as above can be obtained, for example, by the reaction of formaldehyde with isobutene to obtain 3-methyl-3-buten-1-ol and by the reaction of formaldehyde with 2-methyl-2-butene to obtain 2,3-dimethyl-3-buten-1-ol. See, for example, in this regard, commonly assigned U.S. application Serial No. 458,625 filed Apr. 4, 1974, and the references cited therein.

Preferred protonic acids for use in the process of the present invention are hydrogen halide acids such as hydrochloride, hydroiodide, hydrobromide; sulfuric acid; trichloroacetic acid; organic sulfonic acids such as benzene sulfonic acid, toluene sulfonic acid and sulfonated cation exchange resins; phosphoric acid, boron fluoride with methanol, etc. particularly preferred acids are sulfuric and organic sulfonic acids such as the sulfonated cation exchange resins. Preferably the acid has a pKa as measured in aqueous solution at 25°C between 0 and 3, more preferably between 0 and 2. The term pKa is used herein to mean the negative logarithm to the base 10 of the acid ionization constant (Ref. "Textbook of Quantitative Inorganic Analysis" by I. M. Kaltoff and E. B. Sandell, Macmillan Co., NYC, 1947, page 35).

This process may also be carried out in the presence of a solvent. Typical solvents are the polar liquids, e.g., organic solvents such as methanol, acetic acid, tetrahydrofuran, dimethylformamide, etc. Water is also a satisfactory solvent. When using a solvent, it is preferred to use from 1 to 10 parts by volume of a solvent per part of epoxide.

EXAMPLES

Table I below tabulates exemplary data for conversion of epoxides to substituted tetrahydrofurans in accordance with the present invention. Runs 1-3 are concerned with the conversion of 3-methyl-3,4-epoxy-butan-1-ol to 3-methyl-tetrahydrofuran. Runs 4, 5 and 6 are concerned with the conversion of 2,3-dimethyl-3,4-epoxy-butan-1-ol to 3,4-dimethyltetrahydrofuran.

In Run 1, as indicated in Table I, 6 g of the epoxide were charged to a stainless-steel reactor together with 24 g of 1-normal sulfuric acid and a hydrogenation catalyst consisting of 5 weight percent palladium on carbon. The amount of hydrogenation catalyst was sufficient to be 3 weight percent of the mixture in the reactor. As indicated in Table I, the reaction conditions employed included a hydrogen pressure of 1150 psig and a reaction temperature of 100°C. The reaction was carried out by pressuring up the reaction vessel with hydrogen and then bringing it up to the 100°C temperature and holding there for about 1 hour. After the 1-hour reaction time, the mixture was cooled to room temperature, and the hydrogen was released.

The sample was neutralized and then analyzed by vapor-phase chromatography. The mixture was found to contain 55 mol percent of the 3-methyl-tetrahydrofuran product, 3 mol percent of cyclic alcohols, and about 40 mol percent of trialcohols (triols).

In Run 2, 0.6 g epoxide were charged to a 90-cc Fischer-Porter glass reactor together with 2.4 g of 1-normal sulfuric acid and 0.1 g of 5 weight percent palladium on porous carbon.

The reactor was sealed and then it was pressured up to 200 psig with gaseous hydrogen. The temperature was brought up to 100°C in about 1 hour in an oil bath and held for 2 hours. The hydrogen was released, and the contents of the reactor were cooled to room temperature.

After neutralizing a portion of the reactor contents using calcium carbonate, the neutralized portion was analyzed by vapor-phase chromatography. The mixture was found to contain 83 mol percent 3-methyl-tetrahydrofuran.

The remaining reactor contents were again pressured up with hydrogen to a pressure of 100 psig, and the temperature was brought up to 120°C and held for 1 hour. After this further treatment, the mixture was analyzed and found to contain 97 mol percent 3-methyl-tetrahydrofuran. Thus, surprisingly high yields of substituted tetrahydrofuran were obtained by the process of the present invention.

Runs 3, 4, 5 and 6 were carried out similarly under the conditions and with the results as indicated in Table I below.

TABLE I

3-Methyl-Tetrahydrofuran from 3-Methyl-3, 4-Epoxy-butan-1-ol

| Run No. | Epoxide (grams) | Solvent (grams) | Catalyst (Wt.% of Mixture) | Reaction Conditions | | | Products (mol %) | | |
|---|---|---|---|---|---|---|---|---|---|
| | | | | $H_2$ Press. (psig.) | Temp. (°C) | Time (Hr) | 3-Me-THF | Cyclic Alcohol | Triol |
| 1 | 6 | Water (23) | Conc. $H_2SO_4$ (3) / 5% Pd/C (3) | 1150 | 100 | 1 | 55 | 3 | 40 |
| 2 | 0.6 | Water (2.3) | Conc. $H_2SO_4$ (3) / 5% Pd/C (3) | 200 / 100 | 100 / 120 | 2 / 1 | 83 / 97 | 17 / 2 | <1 / <1 |
| 3 | 1 | Acetic Acid | Conc. $H_2SO_4$ (1) / 5% Pd/C (2) | 200 | 120 | 1.5 | 66 | — | — |

TABLE I -continued

3-Methyl-Tetrahydrofuran from 3-Methyl-3,4-Epoxy-butan-1-ol

| Run No. | Epoxide (grams) | Solvent (grams) | Catalyst (Wt.% of Mixture) | Reaction Conditions H₂ Press. (psig.) | Temp. (°C) | Time (Hr) | Products (mol %) 3-Me-THF | Cyclic Alcohol | Triol |
|---|---|---|---|---|---|---|---|---|---|
| | | | 3,4 Dimethyl-Tetrahydrofuran from 2,3-Dimethyl-3,4-Epoxy-butan-1-ol | | | | | | |
| 4 | 6 | Water (23) | Conc. H₂SO₄ (3) / 5% Pd/C (3) | 1140 | 100 | 1 | 80 | — | — |
| 5 | 1 | MeOH (4) | BF₃ (MeOH) (2) / 5% Pd/C (2) | 150 | 100 | 1 | 66 | 33 | <1 |
| 6 | 0.6 | Water (2.3) | Conc. H₂SO₄ (3) / 5% Pd/C (3) | 200 | 100 | 1.8 | 93 | 7 | <1 |

I claim:

1. A process for producing a substituted tetrahydrofuran which comprises contacting an epoxide with molecular hydrogen and a Group VIII metal hydrogenation catalyst at a temperature between 50° and 250°C and a pressure between 10 and 5,000 psig, wherein the contacting is carried out in the liquid phase and in the presence of a protonic acid, and the epoxide has the formula

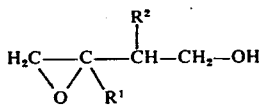

wherein $R^1$ is a methyl, ethyl, propyl or butyl group and wherein $R^2$ is hydrogen, methyl, ethyl, propyl or butyl and wherein the Group VIII metal hydrogenation catalyst comprises iron, cobalt, nickel, ruthenium, rhodium, palladium, osmium, iridium, or platinum, wherein the metal is present in the catalyst in elemental, oxide, or sulfide form.

2. A process in accordance with claim 1 wherein the temperature is between 100° and 150°C and the pressure is between 100 and 1000 psig.

3. A process in accordance with claim 1 wherein the catalyst comprises nickel, palladium or platinum.

4. A process in accordance with claim 1 wherein the epoxide is 3-methyl-3,4-epoxy-butan-1-ol.

5. A process in accordance with claim 1 wherein the epoxide is 2,3-dimethyl-3,4-epoxy-butan-1-ol.

6. A process in accordance with claim 1 wherein the protonic acid is sulfuric, acetic, boron fluoride with methanol, a hydrogen halide acid, trichloroacetic acid or an organic sulfonic acid.

7. A process in accordance with claim 1 wherein the protonic acid has a pKa less than 3.

8. A process in accordance with claim 7 wherein a polar liquid solvent is utilized.

* * * * *